United States Patent [19]
Crittenden

[11] Patent Number: 5,290,247
[45] Date of Patent: Mar. 1, 1994

[54] INTRACORONARY EXCHANGE APPARATUS AND METHOD

[75] Inventor: James F. Crittenden, Hollis, N.H.

[73] Assignee: C. R. Bard, Inc., Murray Hill, N.J.

[21] Appl. No.: 703,603

[22] Filed: May 21, 1991

[51] Int. Cl.⁵ .............................................. A61M 5/00
[52] U.S. Cl. ..................................... 604/171; 604/96
[58] Field of Search ............... 604/171, 164, 170, 96, 604/264, 280, 158, 159, 102

[56] References Cited

U.S. PATENT DOCUMENTS

| | | | |
|---|---|---|---|
| 4,431,426 | 2/1984 | Groshong et al. | 604/164 X |
| 4,606,347 | 8/1986 | Fogarty et al. | 604/102 X |
| 4,762,129 | 8/1988 | Bonzel | 604/96 |
| 4,917,088 | 4/1990 | Crittenden | 604/194 |
| 5,035,686 | 7/1991 | Crittenden | 604/96 |
| 5,041,085 | 8/1991 | Osborne et al. | 604/171 X |
| 5,147,335 | 9/1992 | Wright | 604/264 X |

Primary Examiner—Gene Mancene
Assistant Examiner—Jeffrey A. Smith
Attorney, Agent, or Firm—Morgan & Finnegan

[57] ABSTRACT

An intracoronary sheath for use in catheter exchanges has an elongate tubular body with a proximally facing funnel at the proximal end of the sheath. A proximally extending wire for manipulating the sheath is attached to the proximal end of the sheath. The intracoronary sheath is advanced by manipulation of the wire over a first catheter positioned in a guide catheter and extends beyond the distal end of the guide catheter into the patient's vascular system. After the first catheter is removed, a second catheter advanced through a guide catheter is guided by the funnel into the intracoronary sheath and through the vascular system to a desired position in the patient's body. A second embodiment provides for the exchange of a second guidewire for a first guidewire. A first guidewire is positioned within a monorail-type catheter extending into the patient's vascular system. The monorail type catheter is provided with a proximally facing funnel on a proximally facing opening leading into the lumen of the monorail catheter which receives the guidewire. After the first guidewire is removed, the second guidewire introduced. The funnel guides the guidewire into the proximally facing opening and then into the guidewire lumen of the monorail-type catheter.

28 Claims, 7 Drawing Sheets

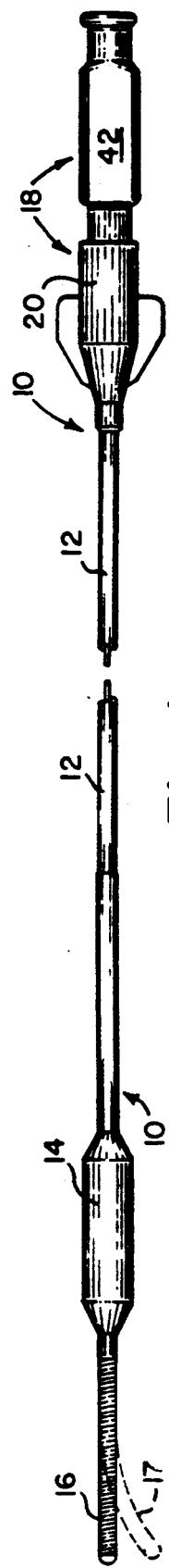
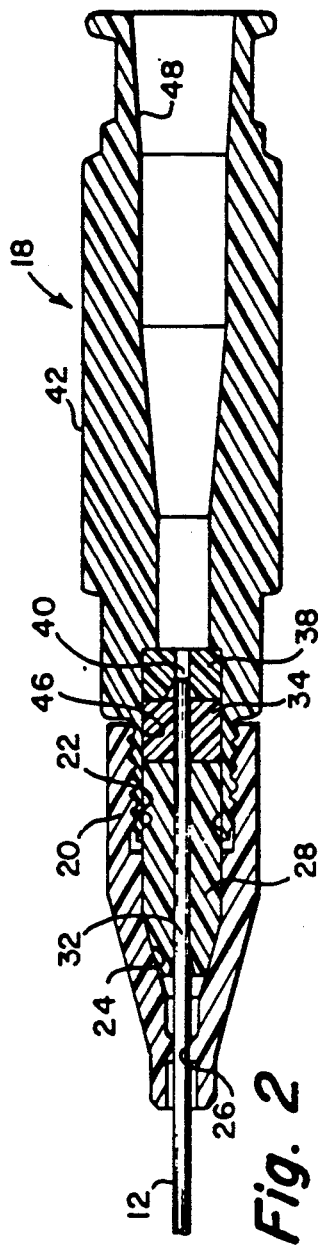
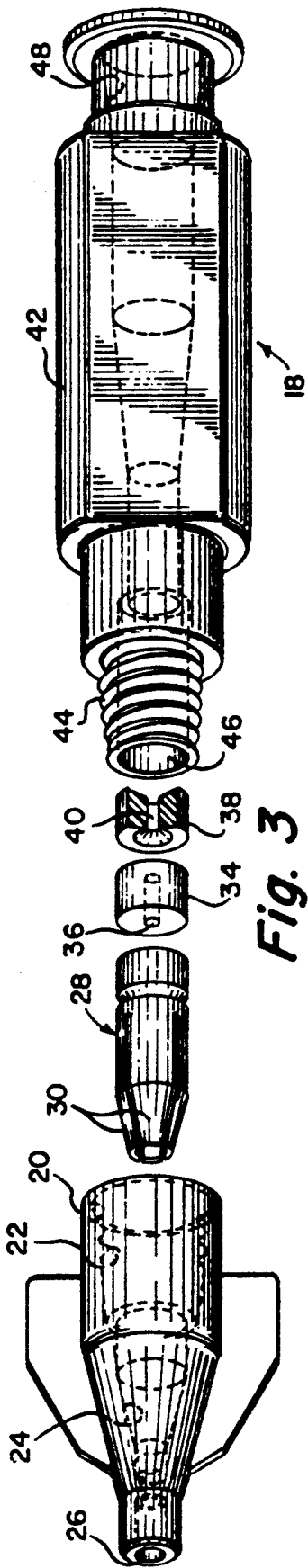
Fig. 1
Fig. 2
Fig. 3

INTRACORONARY EXCHANGE APPARATUS AND METHOD

FIELD OF THE INVENTION

This invention relates to improvements in catheter exchanges between one type of catheter, such as an over the wire percutaneous transluminal coronary angioplasty (PTCA) catheter and a fixed wire catheter or between two fixed wire catheters without losing the ability to position the succeeding catheter quickly in the stenosis being treated. The invention also relates to guidewire exchanges, in which one guidewire may be substituted for another in a monorail type catheter without losing the position of the monorail catheter in the patient's body.

BACKGROUND OF THE INVENTION

This invention relates to improvements in devices and techniques used with small diameter low profile dilatation angioplasty catheters, particularly in coronary angioplasty. More particularly, the invention concerns improvements in systems for effecting catheter exchanges when one of the catheters is of the "fixed wire" type which incorporates a wire-like shaft that is sufficiently torsionally rigid so as to be steerable thereby enabling the catheter to be selectively guided and steered to the desired location in the patient's coronary arteries.

In performing coronary angioplasty, it often occurs that the physician may wish to use a catheter different than the one originally inserted into the patient. For example, this may occur if the initial selection of catheter balloon size was inappropriate to treat the patient's stenosis or some other event occurs that would make use of a different catheter desirable. When the catheter is of the type that uses a separate movable guidewire, the catheter may be exchanged in a well known procedure in which an exchange wire is substituted for the movable guidewire (or the length of the guidewire is extended with an extension wire); then the catheter is withdrawn over the exchange wire and the replacement catheter is threaded over the exchange wire and is thereby guided to the stenosis. By maintaining the guidewire in position during the exchange procedure, the replacement catheter is easily and quickly advanced to the stenosis.

The foregoing catheter exchange procedure has not been usable with small diameter low profile dilatation catheters of the type that incorporate an integral guidewire because the balloon catheter cannot be separated from the guidewire. Thus, when it is desired to exchange one such dilatation catheter for another, the typical procedure is to withdraw the entire catheter and integral guidewire and then replace it with the desired catheter. Withdrawal of the catheter, however, results in loss of position of the catheter in the stenosis. As a result, the next placed catheter must be re-manipulated through the patient's arterial system to position the balloon in the stenosis. The replacement of the catheter typically involves time consuming manipulation and steering to guide the catheter to place its balloon within the stenosis. The additional procedure increases somewhat the risk of trauma to the patient.

A similar problem is presented when it is desired to exchange a conventional movable guidewire dilatation catheter for a catheter of the type having an integral guidewire. Again, in order to make such an exchange, it has been customary to remove completely the movable guidewire and the dilatation catheter to permit insertion of the integral guidewire type of catheter. Because there is nothing to guide the catheter directly to the stenosis, it is necessary for the physician to go through all the manipulations necessary to steer and guide the new catheter to the stenosis.

A problem again occurs in the use of a monorail type catheter. It may be desired to exchange the indwelling guidewire with another guidewire of a different size or stiffness. Presently, if the guidewire is removed with the monorail catheter, the replacement guidewire must be re manipulated back through the patient's arterial system, a time consuming task. If the monorail catheter is left in place and only the guidewire removed, it is not possible to re-manipulate and steer the replacement guidewire to the opening or entry port of the lumen of the monorail which accepts the guidewire because the entry port or opening is of small diameter and of unsuitable orientation.

It would be desirable, therefore, to provide a system by which guidewire exchange may be facilitated with the use of a monorail-type catheter.

It would be desirable, therefore, to provide a system by which catheter exchanges involving small diameter low profile dilatation catheters having an integral guidewire could be effected easily, quickly, without loss of position and with minimal trauma. It is among the objects of the invention to provide such a system.

SUMMARY OF THE INVENTION

The intracoronary sheath of the present invention is used with a small diameter coronary dilatation catheter having a shaft formed from stainless steel hypodermic tubing. The distal end of the shaft is of increasing flexibility and terminates in a highly flexible distal tip. A dilatation balloon is mounted to the shaft near the distal end. The interior of the balloon is in communication with the lumen extending through the hollow shaft. The balloon may be inflated and deflated with a liquid by a syringe or other suitable inflation device attached to the proximal end of the shaft by a luer fitting carried at the proximal end of the shaft. The luer fitting is detachable from the hypodermic tubing so as to present a smooth continuous diameter at the proximal end of the catheter shaft. The luer fitting includes a collet and nut arrangement by which the luer fitting can grip securely the tubular proximal end of the dilatation shaft.

In order to introduce the intracoronary sheath of the present invention over the dilatation catheter, the luer fitting must first be detached from the catheter. After the luer fitting is detached, the intracoronary sheath of the present invention is placed over the catheter shaft and advanced through the guide catheter. The guide catheter will have been already previously positioned such that it leads to the entrance to the coronary artery. The intracoronary sheath is attached to a relatively stiff wire-like shaft that is attached to and extends proximally of the proximal end of the intracoronary sheath. A flexible funnel attached at the proximal end of the intracoronary sheath is made of a material capable of collapsing or folding such that it easily passes through the Y-connector of the guide catheter. By advancing the wire-like shaft, the distal end of the intracoronary sheath is moved out of the guide catheter and into the coronary artery itself until it reaches a desired location at the stenosis near the tip of the fixed wire catheter.

The fixed wire catheter then may be withdrawn through the intracoronary exchange sheath, through the guide catheter and out of the patient. A replacement guidewire or catheter may next be introduced through the guide catheter, until it reaches the funnel. The funnel guides the replacement guidewire or catheter into the intracoronary sheath which, in turn, guides the catheter or guide wire. The sheath is dimensioned in length such that even in its most extended position, the proximal end of the sheath is positioned proximal of the aortic arch. The intracoronary sheath may then be removed by pulling it over the replacement device by the wire-like shaft, thus leaving the replacement device in the desired location within the body. The funnel may be perforated to allow the infusion of contrast fluids through the guide catheter, or to allow pressure monitoring of the patient.

The guiding capability provided by the funnel applied to the intracoronary sheath may be suitably adapted for use with a monorail-type catheter. Typically, a monorail-type catheter is contained within a guide catheter which is in turn positioned in the patient. This capability is accomplished by providing a proximally-facing funnel in the vicinity of and around the periphery of the monorail-type catheter's entry port or opening provided for receiving a guidewire. The guidewire to be exchanged is removed by withdrawing it out of the guide catheter, while maintaining the monorail-type catheter in place. Then, the replacement guidewire is manipulated through the guide catheter in a direction towards the entry port or opening of the monorail catheter. Upon reaching the proximally facing funnel, the guidewire will be guided into the entry port or opening and subsequently into the guidewire lumen in the monorail-type catheter. As in the intracoronary sheath embodiment, the funnel may be perforated to allow the infusion of contrast fluids through the guide catheter.

It is among the general objects of the invention to provide an improved system for performing catheter exchanges involving a small diameter dilatation catheter having an integral guidewire.

Another object is to provide a movable sheath which is advanced and positioned within the guide catheter to facilitate catheter exchanges without losing the catheter's position within the body.

Yet another object is to provide a guide on a monorail catheter which facilitates guidewire exchanges without disturbing the position of the catheter.

DESCRIPTION OF THE DRAWINGS

The foregoing and other objects and advantages of the invention will be appreciated more fully from the following further description thereof with reference to the accompanying drawings wherein:

FIG. 1 is a fragmented illustration of a small diameter dilatation catheter having an integral guidewire-like shaft:

FIG. 2 is an enlarged cross sectional illustration of the proximal end of the dilatation catheter shaft and the luer fitting;

FIG. 3 is an exploded illustration of the luer fitting;

DESCRIPTION OF THE ILLUSTRATIVE EMBODIMENTS

Figure 4A:
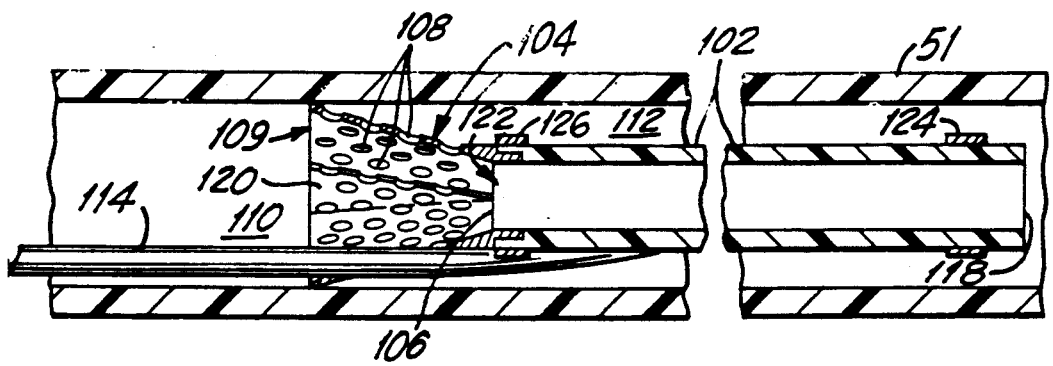
FIG. 4A is a diagrammatic illustration of an intracoronary sheath in accordance with the invention having its proximal end positioned within the guide catheter and its distal end extending distally toward the coronary artery, in readiness to receive and guide a newly-introduced catheter.

FIG. 1 illustrates, generally, a fixed-wire type of small diameter balloon dilatation catheter 10 with which the present invention is particularly useful. The catheter may be of the order of 175 cm long. It includes an elongate shaft 12 formed from hypodermic tubing. A polymeric dilatation balloon 14 is mounted to the distal end of the catheter. The distal tip 16 of the catheter is of increasing flexibility in a distal direction and, typically, may include a helical coil of radiopaque material. The shaft 12 is sufficiently torsionally rigid so that it may transmit rotation from the proximal to the distal end of the catheter when the distal end is in the coronary arteries. In order that the device may be selectively steered through the branches of the coronary anatomy, the distal tip 16 is adapted to be bent to a slight "J" shape illustrated in phantom at 17. A luer fitting 18 is attached to the proximal end of the shaft 12 to enable attachment of an inflation device such as a syringe (not shown) to inflate and deflate the balloon 14 with a suitable fluid, such as radiopaque contrast liquid. Such a catheter is disclosed in more detail in U.S. Pat. No. 4,917,088 issued Apr. 17, 1990.

As shown in FIGS. 2 and 3, the luer fitting, indicated generally at 18, includes a hub 20 having a socket 22 at its proximal end and a distally tapering bore 24 located distally of the socket 22. An aperture 26 is formed at the distal end of the hub 20 and receives the proximal end of the catheter shaft 12. A collet 28 having distally extending fingers 30 is provided with a central bore 32, also to receive the proximal end of the shaft 12 of the catheter. A compressible gasket 34 formed from an elastomeric material such as silicone rubber, and also provided with a central bore 36, abuts the proximal face of the collet 28. The bore 36 of the gasket 34 receives the proximal end of the catheter shaft 12. A shaft stop member 38 is provided with a central aperture 40 which tapers in a proximal direction. The bore 40 tapers to a diameter that is smaller than the diameter of the proximal end of the catheter shaft 12 and, therefore, serves as an abutment for the proximal end of the shaft 12 as shown in FIG. 2, to prevent it from extending proximally beyond the stop member 38. The collet 28, gasket 34 and stop member 38 are securely retained between the hub 20 and a luer body 42 having a threaded distal end 44 that screws into the socket 22 of the hub 20. The distal end of the luer body 42 has a socket 46 which receives stop member 38, the gasket 34 and the proximal portion of the collet 28. The distal fingers 30 of the collet bear against the tapered bore 24 in the nut. When the luer body 42 is screwed into the nut 20, the collet fingers 30 constrict about the proximal end of the shaft 12 to securely lock the luer fitting 18 in place. The gasket 34 also is compressed to effect a secure liquid seal about the shaft 12. The proximal end of the luer body 42 has a luer socket 48 adapted to be connected to a syringe or other inflation/deflation device. Thus, it will be appreciated that the entire luer fitting 18 may be detached from the proximal end of the shaft 12 simply by unscrewing the hub 20 and luer body 42 to release the collet and permit the assembly to slide off of the proximal end of the shaft 12.

Figure 5:
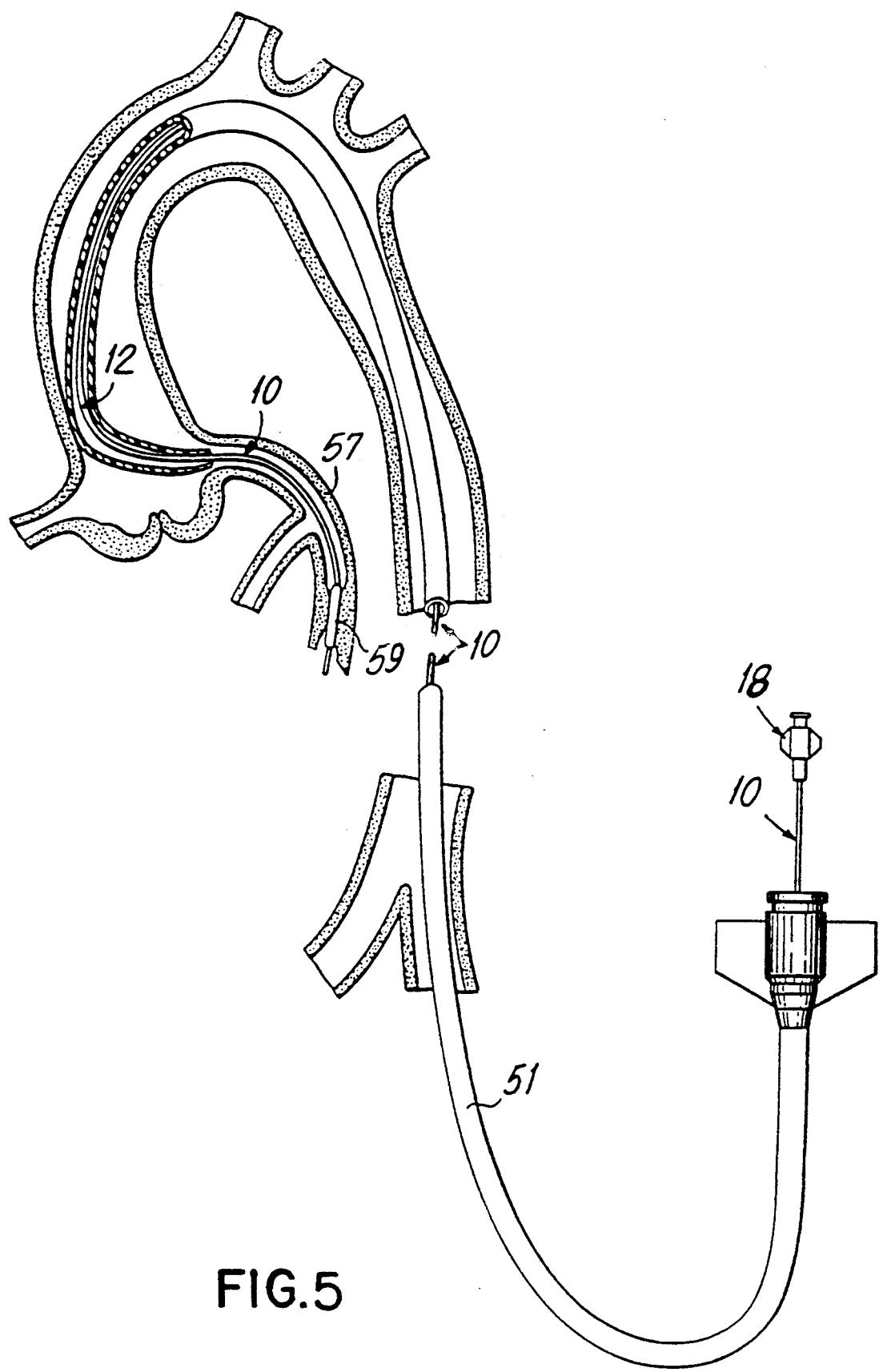
FIG. 5 is a fragmented illustration of a coronary arterial system with a guide catheter in place and a dilatation catheter having a detachable luer fitting extending through the guide catheter and into the stenosis of a coronary artery.

FIG. 5 illustrates a guide catheter 51 in place in the patient's arterial system and a small diameter dilatation catheter 10 extending through the guide catheter 51, into a coronary artery 57 and into the stenosis 59. A catheter exchange requires removal of the initial catheter 10.

Figure 4B:
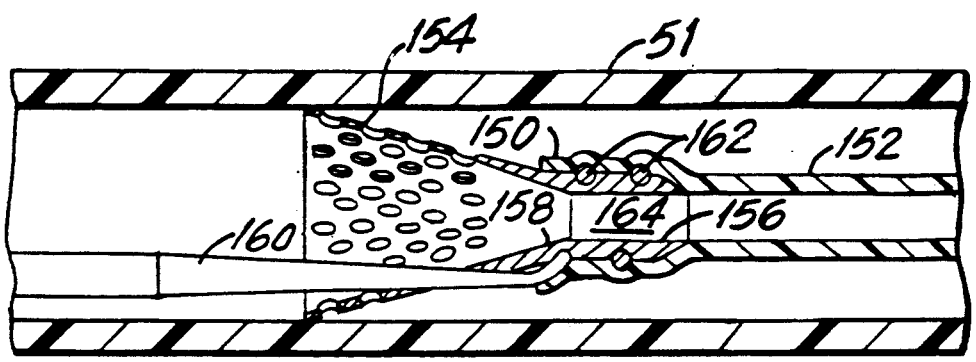
FIG. 4B is a diagrammatic illustration of an alternative embodiment of the intracoronary sheath of FIG. 4A.
Figure 6:
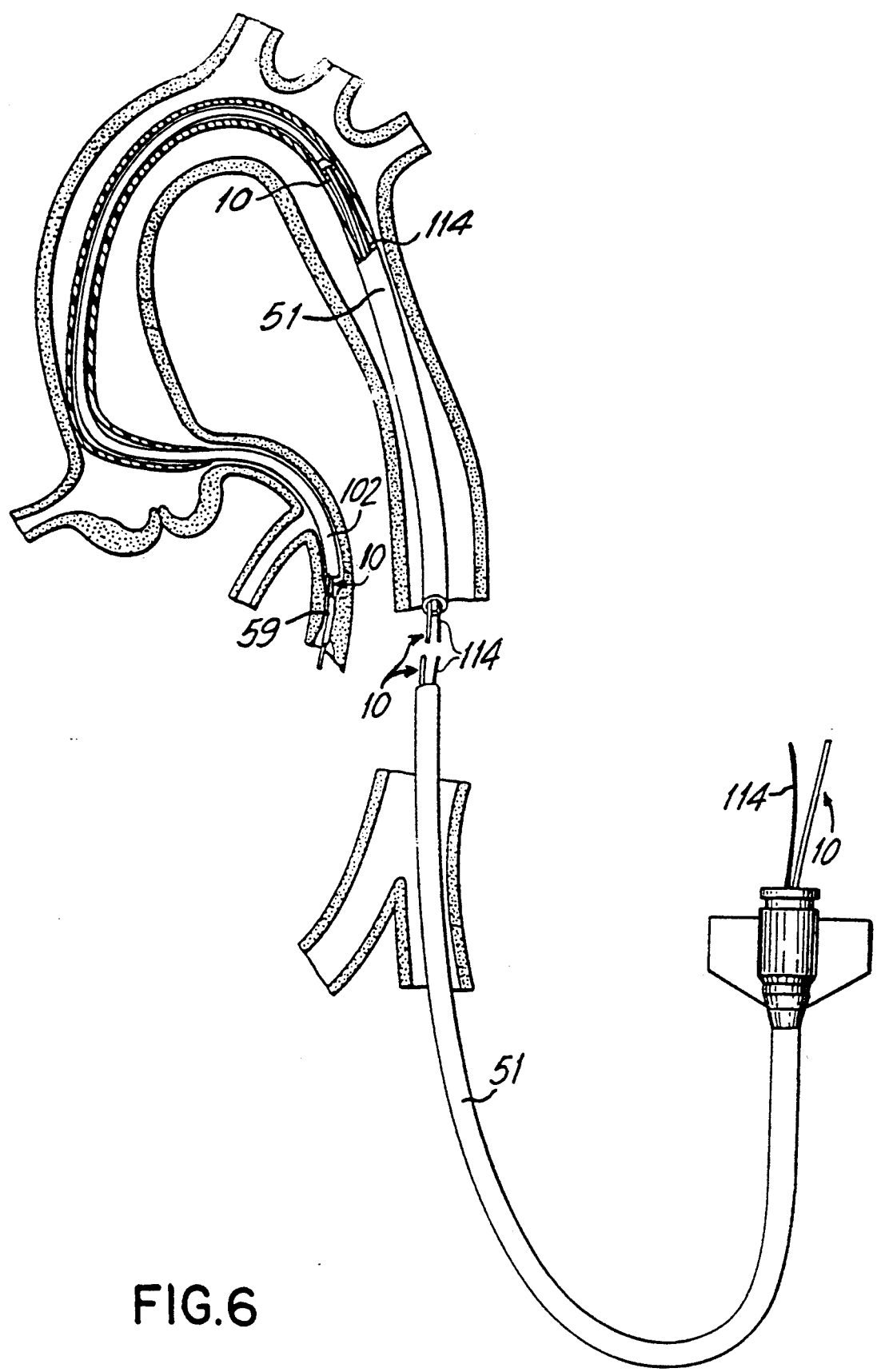
FIG. 6 is an illustration similar to FIG. 5 with the proximal luer fitting of the catheter detached, and the exchange sheath advanced over the balloon dilatation catheter and into the coronary artery in proximity to the stenosis.

In the mode of operation illustrated in FIG. 5, the luer fitting 18 is first detached from the catheter shaft by unscrewing the luer body to loosen the fitting 18. Removal of luer 18 leaves the catheter shaft 12 of FIG. 5 available to act as a guide for the exchange sheath of the present invention. The present invention illustrated in FIGS. 4A and 4B provides an intracoronary sheath 102 having proximal and distal ends. For purposes of the present discussion, it suffices that the sheath 102 is understood as being used with a guide catheter in the manner shown by FIG. 5. Referring now to FIG. 4A, the sheath 102 is a generally solid tubular member having two open ends and is proportioned to be of a diameter generally less than the diameter of a guide catheter 51. The sheath 102 may be constructed of lengths ranging from about 15 cm. to, more advantageously, 35 cm. The latter length is more advantageous because, for an average person, constructing the sheath of length 35 cm. assures that the sheath may extend, in its extreme extended position into the coronary artery as illustrated in FIG. 6 and proximally back over the aortic arch as also shown in FIG. 6. In this manner, the wire 114 will extend proximally of the aortic arch as well, thus making unnecessary the bending of the relatively stiff wire 114 around the aortic arch. However, it is not required that the sheath be so dimensioned since the funnel can approach to the distal end of the guide catheter and function as desired.

Figure 9A:
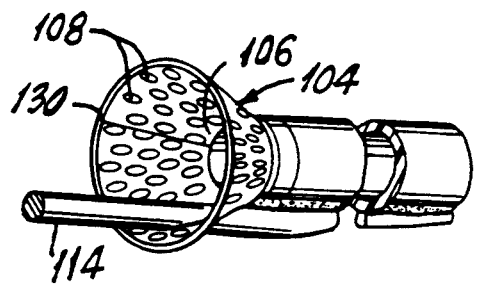
FIGS. 9A and 9B illustrate an alternative embodiment of the funnel associated with the exchange sheath.

It is important that the sheath not be advanced so far that the sheath and its attached funnel pass out of the tip 116 of the guide catheter 51. This event is prevented by sizing the wire 114 of a length, preferably less than 100 cm., so that its extension outside the body, when the sheath is fully inserted in a manner shown in FIG. 6, is minimal, thus preventing further advancement of the sheath. The wire 114 preferably may be made of stainless steel and preferably 0.020 inch in diameter. The sheath 102 preferably has an outside diameter of 0.060 in. and 0.050 inch inside diameter and may be constructed of high density polyethelene. The funnel 104 may be constructed of the same material and heat bonded to the sheath. As shown in FIG. 9A, the wire 114 may be attached to sheath 102 through a hole or perforation 128 in the cone 104. The wire may be tapered down at the point of its attachment to sheath 102 and may be wrapped around sleeve 102 to secure it to the sleeve by suitable bonding. The portion of wire 114 wrapped around sheath 102 may be radiopaque coated to act as a fluoroscopic marker in lieu of or in conjunction with a radiopaque marker band 126. The funnel's narrow opening 106 is mounted to the proximal end of the sheath 102 and the larger opening 109 of funnel 104 extends proximally of the narrow opening. The funnel 104 is perforated with one or more holes or slots 108 which are sized such that fluids in passage 110 may pass through perforations 108 to passage 112 in the guide catheter 51. The perforations thus permit the passage of fluids through the guide catheter 51 and into the person's body and permit monitoring of blood pressure in the person's body. The perforations 108 permit free passage of fluids through the funnel but are sized small enough (on the order of 0.008 inch in diameter for a circular perforation and 0.008 by 0.020 inch for a slotted perforation) so a catheter cannot enter any of the perforations 108. The number of perforations in the funnel are preferably chosen such that the total area of the perforations is at least equal to the cross-sectional area of the guide catheter to assure free fluid flow through the funnel. The outer diameter of the large opening 109 of funnel 104 is of a dimension such that it fits snugly within the guide catheter 51 yet can be passed through the guide catheter 51 without excessive effort.

FIG. 4B illustrates an alternative embodiment of an intracoronary sheath. In FIG. 4B, sheath 152 is flared at its proximal portion 150. The funnel 154 has an elongated distal extension portion 156 which extends from the distal end 158 of the funnel 154 and is inserted into the flared proximal portion 150 of the sheath 152. In addition, a wire-like shaft 160, of similar construction and material to wire-like shaft 114, at its distal end is wound into a spiral section 162 and wrapped around the distal portion 156 of the funnel 154. The spiral section 162 may be incorporated into a heat bond formed between the proximal portion 150 of the sheath 152 and the distal extension portion 156 of the funnel 154. This provides a highly reliable, secure attachment of the wire 160 to both the sheath 152 and funnel 154. In the embodiment of FIG. 4B, radiopaque marking can be accomplished by plating the spiral section 162 with a dense metal (e.g., gold) or alternatively a short spiral of dense metal wire may be interfitted with the stainless steel wire 160 in bifilar fashion. In assembling the sheath 152 with funnel 154 and spiral section 162, first heat shrink tubing (not shown) of known construction is used as a compression tool over the flared portion 150. A mandrel wire (not shown) of known construction and use is inserted into an opening 164 in the funnel and supports the interior walls of the funnel 154. The wire maintains a smooth inner diameter during the compression heat bonding. After the bonding is completed, both the mandrel wire and shrink tubing are removed, thus leaving the flared portion of the sheath heat bonded to the funnel and spiral wire.

Figure 11:
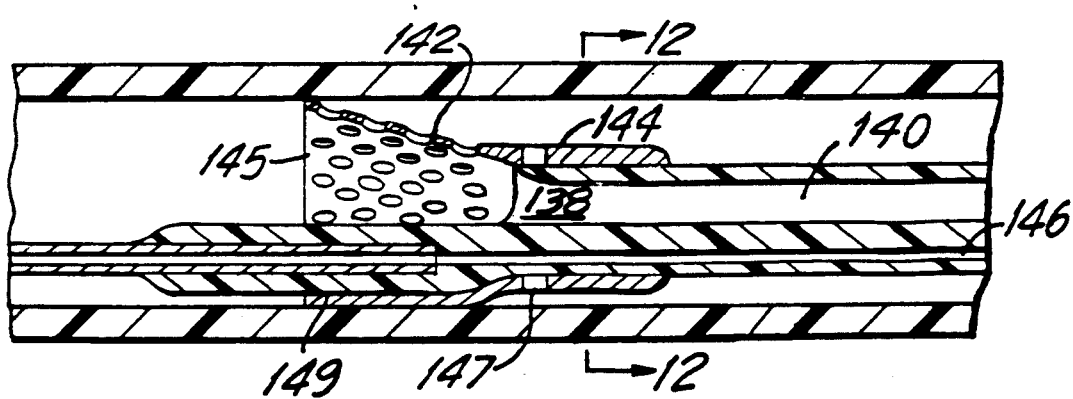
FIG. 11 is an enlarged partial sectional illustration of the catheter of FIG. 10 modified with the funnel of the present invention.

In an alternative construction, the positions of the funnel and sheath just described in reference to FIG. 4B may be reversed. The funnel may be constructed of sufficiently large diameter to be fitted over the sheath. In order to secure the spiral wire wrapped around the funnel, a section of conventional heat shrink tubing would be fitted over the funnel and permanently attached to the funnel to secure the funnel and spiral wire to the sheath. The spiral wire section 162 may be eliminated altogether and, as in FIG. 4A, the wire 160 may be straight tapered and bonded to the sheath with an adhesive such as methylcyanoacrylate or ultraviolet curing adhesive, such as Loctite Corporation's UV—350 product. While the funnels of FIGS. 4A and 4B are shown as being generally centrally-disposed within a guide catheter, the funnels may be offset from their central position and constructed in a manner similar to that to be described below in reference to FIG. 11 of the present invention. While the funnel of FIG. 11 is attached to a monorail-type catheter, the funnel in this alternative embodiment would be attached to a sheath similar to the sheath 102 of FIG. 4A or sheath 152 of FIG. 4B.

In order to advance the intracoronary sheath 102 through the guide catheter 51 and to position it within the guide catheter, a wire-like shaft 114 is attached towards the proximal end of the sheath 102, as shown in FIG. 4A distally of the funnel 104. The wire-like shaft is sufficiently long to extend proximally through the guide catheter to the outside of the body so that the sheath may be advanced and positioned by manipulation of the proximal end of the wire 114 yet short enough, as described above, such that when the sheath is fully inserted as shown in FIG. 6, the length of wire 114 outside the body is minimal to prevent further advancement of the sheath 102.

In operation, when it is desired to perform a catheter exchange, the luer 18 is disconnected as described. At this point the catheter (see catheter 10 in FIG. 5) remains in place. The operator then threads the distal end of the sheath 102 onto the proximal end of the catheter 10 and advances it along the length of the catheter in a monorail fashion. Once the length of the sheath and funnel are within the proximal end of the guide catheter 51, the wire 114 is gripped and pushed, thus advancing the sheath through the distal tip 116 of the guide catheter 51. When the advancing is completed, the tip 118 of the sheath should be positioned in the desired location, for example, in the area of the stenosis 59 as shown in FIG. 6.

Figure 8A:
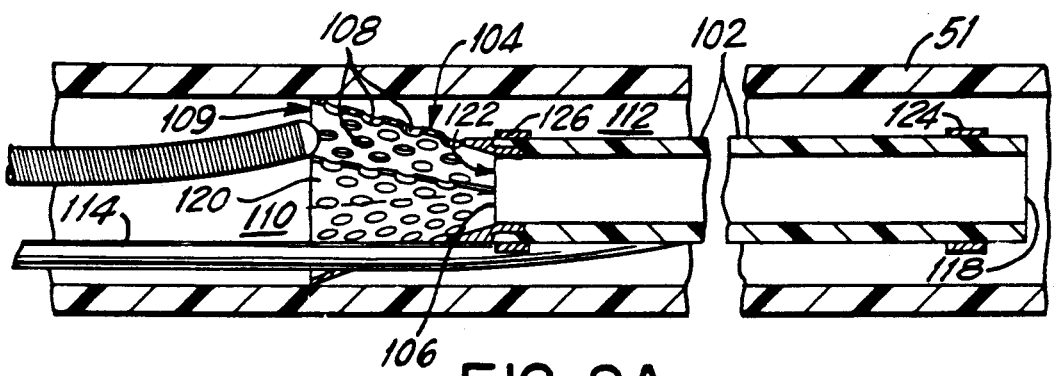
FIGS. 8A and 8B are partial sectional illustrations of a portion of the guide catheter and showing the guiding of a new catheter into the sheath after it has been positioned within the guide catheter.
Figure 8B:
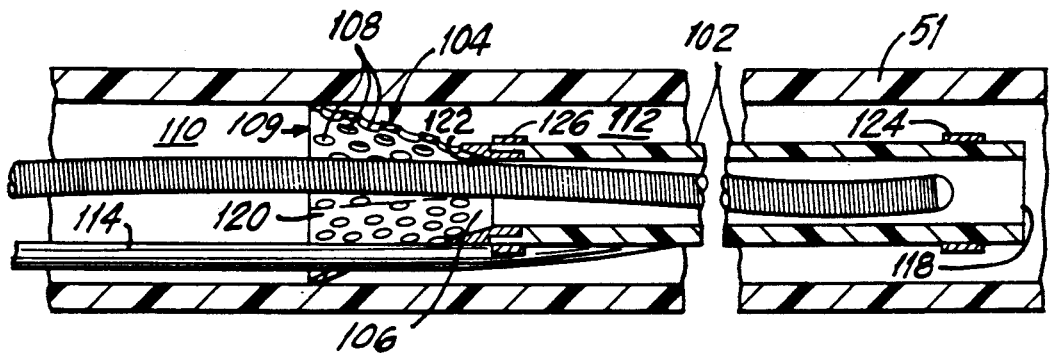
Figure 7:
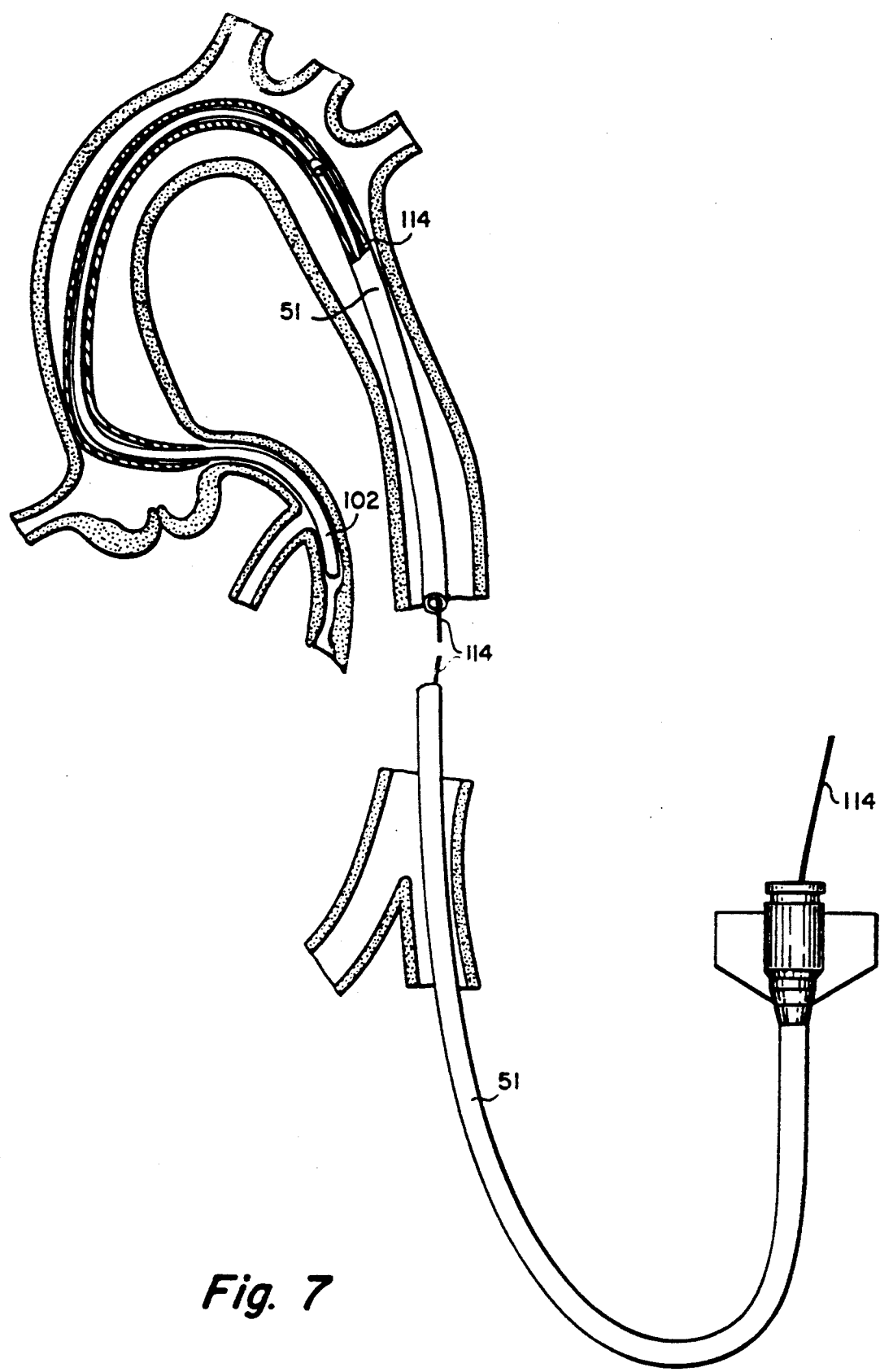
FIG. 7 is an illustration of the arterial and catheter system of FIG. 6 with the dilatation catheter removed, leaving the exchange sheath in place and in readiness to receive another dilatation catheter having an integral guidewire.

After the positioning, the catheter 10, which may be a fixed wire or other catheter, may be removed by withdrawing it in the conventional manner. This action leaves the sheath in place and allows the operator to advance another catheter of any suitable type through the guide catheter 51 as shown in FIG. 7. As illustrated in FIGS. 8A and 8B, upon reaching the larger funnel opening 109, the tip of the advancing catheter may be centered within the guide catheter 51 and thus advance directly into sheath 102. If not centered, the tip of the advancing catheter will be guided by the inner inclined walls 120 of funnel 104 to the opening 122 at the proximal end of sheath 102 and thence through the sheath and to the desired position within the coronary artery. After the new catheter has been positioned as desired, the sheath may be removed or remain in place to permit further catheter exchanges.

Figure 9B:
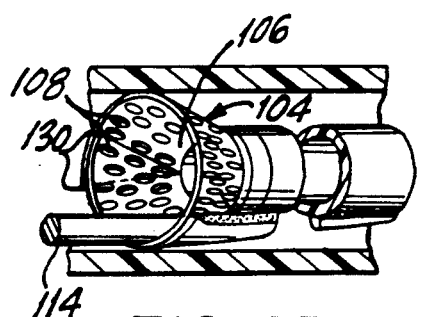

While in the preferred embodiment shown in FIG. 4A a funnel has been shown and described, any other suitably-shaped guide may be used. The funnel 104 may be more elongated with a higher length to diameter proportion. A funnel so constructed allows a greater number of perforations in the funnel, further lessening resistance to fluid flow between passage 110 and passage 112 of the sheath. Further, while a funnel with relatively uniformly inclined walls is shown in FIG. 4, it may be formed in a suitable convex or concave shape. In order to accommodate different diameter guide catheters, the funnel may be slit by one or more slits 130 cut through the funnel body and extending along its length completely or partially from larger opening 109 to smaller opening 106, as shown in FIGS. 9A and 9B. As illustrated in FIG. 9A, when the cone 104 is in a guide catheter whose diameter approximates that of the outer funnel diameter 109, there is no overlapping of the funnel portions over slit 130. When, however, the guide catheter diameter is smaller than the diameter 109 of the outer funnel, then the slit will permit the funnel ends to overlap, as shown in FIG. 9B. The funnel may be injection molded for resulting uniform wall thickness. Although the funnel and the sheath may be made of one piece construction, preferably the two pieces are separately constructed and heat bonded together. The radiopaque marker or band 126 may be incorporated in the heat bond between the sheath and funnel. The funnel may be constructed without holes or perforations. In such construction, a contrast or other fluid may be directed, from the guide catheter by the solid funnel through the sheath 102 and directly to a body lumen at or adjacent to the distal end 118 of sheath 102. Further, to assist in the positioning of the sheath 102, both at its distal end and in the region of its proximal end, radiopaque bands may be utilized respectively on the distal tip 118 and on the proximal end of sheath 102, shown respectively as bands 124 and 126.

Figure 12:
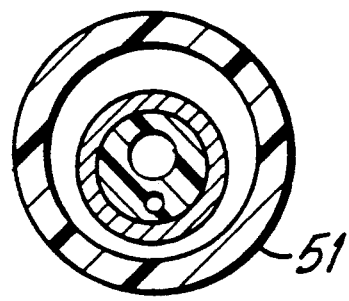
FIG. 12 is a cross sectional illustration of the opening into the lumen of the catheter as seen along the line 12—12 of FIG. 11.
Figure 10:
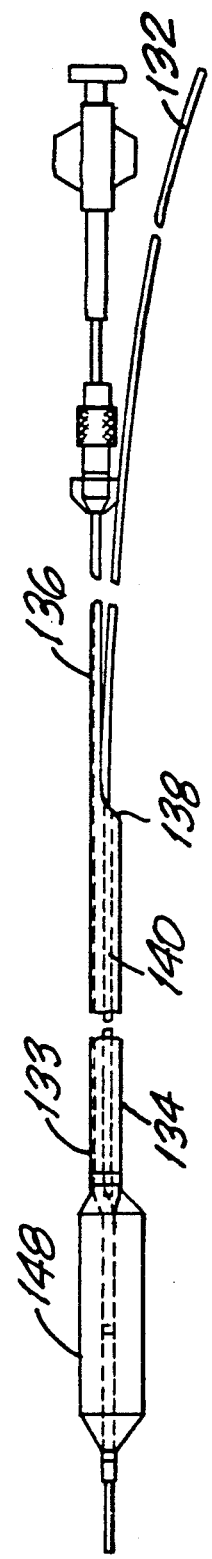
FIG. 10 is an illustration of a monorail-type catheter.

FIGS. 10, 11 and 12 show the invention of the present application applied to rapid exchange two lumen monorail catheters of a type disclosed in Ser. No. 618,531, filed Nov. 26, 1991, now abandoned, for a "Rapidly Exchangeable Coronary Catheter", assigned to the assignee of the present application, the disclosure of which is incorporated herein by reference. As shown in FIG. 10, a guidewire 132 is shown inserted into the distal portion 134 of a catheter 133 which also has a proximal portion 136. In this monorail-type catheter, as shown in FIG. 10, the guidewire lumen 140 extends only over a relatively short length of the catheter at the distal end of the catheter. Because the guidewire lumen 140 is shorter than the portion of the guidewire that protrudes out of the patient, as shown in FIG. 10, some part of the guidewire is always exposed and may be grasped to maintain guidewire position. An advantage of the monorail system is that it is unnecessary to use exchange wires or other devices to increase the effective length of the guidewire in order to perform a catheter exchange. Thus, the monorail-type catheter facilitates introduction of the catheter into the patient's body, as well as exchange of one balloon catheter of this type for another, differently sized, balloon catheter of the same type. However, if it is desired to exchange the guidewire for another guidewire of different stiffness or diameter, for example, it has been heretofore not possible to do so without removing the catheter as well (and thus causing a loss of position of the catheter). Alternatively, the guidewire may be removed without removing the catheter, but introduction of a new guidewire into the monorail catheter is not possible because the guidewire cannot be guided into the distal portion 134 of the catheter 133 by threading it into the opening 138 formed in the proximal end in the guidewire lumen 140, as shown in FIG. 10.

The present invention facilitates the introduction of a guidewire into the catheter 133 by providing a funnel 142 similar to the funnel 104 of FIG. 4A with the smaller opening 144 attached to the proximal end of the distal portion 134 of catheter 133 in a position surrounding opening 138, as shown in FIGS. 11 and 12 and the large opening 145 extending proximally of the smaller opening 144. In FIG. 12, while lumen 138 accepts a guidewire, an additional lumen 146 is provided for inflation and deflation of balloon 148. With the provision of the funnel 142 of FIG. 11, an advancing guidewire will be guided into the opening 138. In operation, the catheter 133 will be contained within a guide catheter 51 of the same type shown in FIG. 5. The catheter 133 will, in use, extend out of the guide catheter by a distance desired. For example, as in FIG. 5, the balloon 148 of catheter 133 may be positioned in or near a stenosis within the patient. The guidewire in place will be removed by pulling on the proximal end thereof. The distal end of the guidewire will exit from the opening 138 in lumen 140 and then be removed from the body. The new guidewire to be inserted into the catheter 133 will then be introduced into and through guide catheter 51 towards opening 138. As the guidewire approaches the opening 138, it will be guided by the funnel 142 into the opening 138 and onward through the guidewire lumen 140 of the catheter until positioned as desired in the patient. As with funnel 104, funnel 142 may be perforated, dimensioned, constructed and slit in the various ways described above with reference to the funnel 104. The funnel 142 may be attached to the catheter, as shown in FIG. 11, by compression heat bonding as described with reference to the bonding of the funnel in the embodiment of FIG. 4B. A radiopaque band 147 may be incorporated into the bond to allow fluoroscopic observation of the funnel 142 within guide catheter 51.

As shown with reference to FIG. 11, the funnel 142 is offset with respect to the catheter 133. This offset construction prevents an approaching guidewire from becoming misdirected to the side of the funnel no leading to the opening 138. In order to further facilitate proper guiding of an approaching guidewire, the side of the funnel 142 not leading to the guidewire lumen may be bonded by suitable means shown at 149 to the surface of the catheter shaft to ensure that the funnel will be offset and to avoid a pocket being formed by the funnel in which an approaching guidewire may become lodged.

In an alternative embodiment to that of FIGS. 11 and 12 with an offset funnel, the funnel may be constructed to be centrally disposed with respect to the monorail-type catheter. Further, the proximal end of the funnel may be extended proximally to or beyond the most proximal end of the two-lumen portion of the catheter, and therefore proximally of opening 138 seen in FIG. 10.

From the foregoing, it will be appreciated that the invention provides a means by which catheter and guidewire exchanges can be performed quickly and expediently with minimal risk to the patient and without losing catheter or guidewire position. The invention enables such an exchange to be made for a catheter of the type having an integral, non-detachable guidewire as well as for a conventional movable guidewire catheter. Although the foregoing description of the invention has made reference to balloon dilatation catheters, it should be understood that the advantages of the invention also may be used with other catheters having both movable guidewires and integral guidewires. For example, the invention may be practised to effect catheter changes with laser catheters, heater probe catheters and the like.

It also should be understood, however, that the foregoing description of the invention is intended merely to be illustrative thereof and that other modifications and embodiments may be apparent to those skilled in the art without departing from its spirit.

Having thus described the invention what we desire to claim and secure by letters patent is:

1. An improved guidewire exchange apparatus for use in facilitating the substitution of a second guidewire for a first guidewire positioned within a monorail catheter, the monorail catheter having a guidewire lumen passage therethrough and a proximally-facing opening in the lumen passage adapted to receive a guidewire, the improvement comprising means associated with the proximally-facing opening for guiding the second guidewire into the lumen of the catheter while the proximally-facing opening is within a body lumen.

2. The invention of claim 1 wherein the means for guiding comprises a proximally facing funnel, the smaller opening of the funnel being attached to the proximally facing opening in the guidewire lumen, the larger opening being proximal of the smaller opening.

3. The invention of claim 2 wherein the monorail catheter is positioned in a guide catheter and wherein the diameter of the larger opening of the funnel approximates the diameter of the guide catheter.

4. A catheter exchange sheath for use in facilitating the substitution of a second catheter for a first catheter positioned within a guide catheter comprising:
an elongate sheath being of a length shorter than the guide catheter and having distal and proximal ends unattached to the guide catheter;
means associated with the proximal end of the sheath for guiding the second catheter into the elongate sheath;
means for controlling the axial position of the sheath while the second catheter is being substituted for the first catheter.

5. The invention of claim 4 wherein the means for guiding comprises a proximally-facing funnel, the smaller opening of the funnel being attached to the proximal end of the sheath, the larger opening being proximal of the smaller opening.

6. The invention of claim 4 wherein the means for advancing includes a wire attached to the sheath for moving the sheath through the body lumen a body lumen.

7. The invention of claim 4 wherein the sheath is on the order of 35 cm. in length.

8. The invention of claim 4 wherein the diameter of the sheath is less than the diameter of the guide catheter and the diameter of the larger opening of the funnel approximates the diameter of the guide catheter.

9. A catheter exchange sheath comprising:
a sheath adapted to be inserted into a guide catheter and having distal and proximal ends unattached to the guide catheter, the proximal end having a guide means attached thereto, the sheath further having a control means for controlling the axial position of the sheath within the guide catheter while the second catheter is being substituted for the first catheter, the distal end of the sheath when positioned extending out of the guide catheter with the proximal end of the sheath being in the vicinity of the distal end of the guide catheter.

10. The sheath of claim 9 where the guide means comprises a funnel whose larger opening faces proximally of the sheath and whose small opening is secured to the proximal end of the sheath.

11. The sheath of claim 9 where the control means is a wire attached near the proximal end of the sheath and extends proximally of the sheath.

12. A method for performing catheter exchange of a second catheter for a first catheter, the first catheter having a shaft with distal and proximal ends, the first catheter being positioned within a guide catheter, the distal end of the first catheter extending distally of the distal end of the guide catheter and being located in a desired location within a body lumen, the method comprising:
- advancing a sheath having distal and proximal ends unattached to the guide catheter over the proximal end of the first catheter shaft through the guide catheter, the sheath having a means at the proximal end thereof for guiding the second catheter into the sheath;
- positioning the sheath with its proximal end at a desired location within the guide catheter and distal end in the body lumen;
- removing the first catheter shaft from the body lumen;
- advancing a second catheter with distal and proximal ends through the guide catheter,
- guiding the second catheter into the sheath via the guiding means; and,
- advancing the second catheter through the sheath and into the body lumen and locating the distal end of the catheter at the desired location within the body lumen.

13. The method of claim 12 wherein the guiding means comprises a proximally-facing funnel, the smaller opening of the funnel being secured to the proximal end of the sheath, the larger opening being proximal of the smaller opening.

14. The method of claim 12 wherein a wire attached to the sheath extends proximally of the sheath and extends through and beyond the guide catheter, and the steps of advancing and positioning the sheath comprise manipulation of the wire.

15. A method for performing the exchange of a second guidewire for a first guidewire, the first and second guidewires having distal and proximal ends, the first guidewire being contained in a monorail catheter, the first guidewire and monorail catheter being positioned within a guide catheter, the method comprising:
- removing the first guidewire shaft from the monorail catheter by pulling on its proximal end;
- advancing the distal end of the second guidewire through the guide catheter by manipulating its proximal end;
- guiding the second guidewire into the monorail catheter via a guiding means; and,
- advancing the second guidewire through the monorail catheter and locating the distal end of the guidewire at the desired location with respect to the monorail catheter.

16. The method of claim 15 wherein the guiding means comprises a proximally facing funnel, the monorail catheter having a guidewire lumen and a proximally facing opening into the guidewire lumen, the smaller opening of the funnel being secured to the proximally facing opening, the larger opening being proximal of the smaller opening.

17. A method for performing catheter exchange of a second catheter for a first catheter, the first catheter having a shaft with distal and proximal ends, the first catheter being positioned within a guide catheter, the distal end of the first catheter extending distally of the distal end of the guide catheter and being located in a desired location within a body lumen, the method comprising:
- advancing a sheath having distal and proximal ends unattached to the guide catheter over the proximal end of the first catheter shaft through the guide catheter, the sheath having a means at the proximal end thereof for guiding the second catheter into the sheath;
- positioning the sheath with its proximal end at a desired location within the guide catheter and distal end in the body lumen;
- removing the first catheter shaft from the body lumen;
- advancing a second catheter with distal and proximal ends through the guide catheter,
- guiding the second catheter into the sheath via the guiding means; and,
- advancing the second catheter through the sheath and into the body lumen and locating the distal end of the catheter at the desired location within the body lumen; and
- further comprising a proximal fitting at the proximal end of the first catheter, and including the step of removing the proximal fitting from the first catheter prior to the step of advancing the sheath.

18. A catheter exchange sheath for use in facilitating the substitution of a second catheter for a first catheter positioned within a guide catheter comprising:
- an elongate sheath being of a length shorter than the guide catheter and having distal and proximal ends unattached to the guide catheter;
- means associated with the proximal end of the sheath for guiding the second catheter into the elongate sheath;
- means for advancing the sheath through a guide catheter;
- wherein the means for guiding comprises a proximally-facing funnel, the smaller opening of the funnel being attached to the proximal end of the sheath, the larger opening being proximal of the smaller opening; and
- wherein the funnel further comprises at least one perforation.

19. A catheter exchange sheath for use in a facilitating the substitution of a second catheter for a first catheter positioned within a guide catheter comprising:
- an elongate sheath being of a length shorter than the guide catheter and having distal and proximal ends unattached to the guide catheter;
- means associated with the proximal end of the sheath for guiding the second catheter into the elongate sheath;
- means for advancing the sheath through a guide catheter;

wherein the means for guiding comprises a proximally-facing funnel, the smaller opening of the funnel being attached to the proximal end of the sheath, the larger opening being proximal of the smaller opening; and wherein the funnel further comprises at least one slit, extending from the larger opening of the funnel to the smaller opening of the funnel.

20. Apparatus for exchanging a second catheter for a first catheter, the first catheter having a shaft with distal and proximal ends, the first catheter being positioned within a guide catheter, the distal end of the first catheter extending distally of the distal end of the guide catheter and being located in a desired location within a body lumen, comprising:

a sheath adapted to be inserted into the guide catheter over the first catheter and having distal and proximal ends unattached to the guide catheter, the proximal end having attached thereto a means for guiding the second catheter, the sheath further having a control means for advancing the sheath through the positioning the sheath within the guide catheter, the distal end of the sheath when positioned being in the vicinity of the distal end of the first catheter with the proximal end of the sheath being in the vicinity of the distal end of the guide catheter;

means for removing the first catheter shaft by its proximal and from the body lumen;

means for advancing a second catheter with distal end proximal ends through the guide catheter, the guide means guiding the catheter into the sheath; and means for advancing the second catheter through the sheath and into the body lumen and for locating the distal end of the second catheter at the desired location within the body lumen.

21. A method for performing catheter exchange of a second catheter for a first catheter, the first catheter having a shaft with distal and proximal ends, the first catheter being positioned within a guide catheter, the distal end of the first catheter extending distally of the distal end of the guide catheter and being located in a desired location within a body lumen, the method comprising:

advancing a sheath having distal and proximal lends unattached to the guide catheter over the proximal end of the first catheter shaft through the guide catheter, the sheath having a means at the proximal end thereof for guiding the second catheter into the sheath;

positioning the sheath with its proximal end at a desired location within the guide catheter and distal end in the body lumen;

removing the first catheter shaft from the body lumen;

advancing a second catheter with distal and proximal ends through the guide catheter, guiding the second catheter into the sheath via the guiding means; and, advancing the second catheter through the sheath and into the body lumen and locating the distal end of the catheter at the desired location within the body lumen;

wherein the guiding means comprises a proximally-facing funnel, the smaller opening of the funnel being secured to the proximal end of the sheath, the larger opening being proximal of the smaller opening; and further comprising at least one slit extending from the larger opening of the funnel at least partially to the small opening of the funnel.

22. A method for performing catheter exchanger of a second catheter for a first catheter, the first catheter having a shaft with distal and proximal ends, the first catheter being positioned within a guide catheter, the distal end of the first catheter extending distally of the distal end of the guide catheter and being located in a desired location within a body lumen, the method comprising;

advancing a sheath having distal and proximal ends unattached to the guide catheter over the proximal end of the first catheter shaft through the guide catheter, the sheath having a means at the proximal end thereof for guiding the second catheter into the sheath;

positioning the sheath with its proximal end at a desired location within the guide catheter and distal end in the body lumen;

removing the first catheter shaft from the body lumen;

advancing a second catheter with distal and proximal ends through the guide catheter, guiding the second catheter into the sheath via the guiding means;

advancing the second catheter through the sheath and into the body lumen and locating the distal end of the catheter at the desired location within the body lumen;

wherein the guiding means comprises a proximally-facing funnel, the smaller opening of the funnel being secured to the proximal end of the sheath, the larger opening being proximal of the smaller opening; and wherein the funnel further comprises at least one perforation.

23. An improved guidewire exchange apparatus for use in facilitating the substitution of a second guidewire for a first guidewire positioned within a monorail catheter, the monorail catheter having a guidewire lumen passage therethrough and a proximally-facing opening in the lumen passage adapted to receive a guidewire, the improvement comprising means associated with the proximally-facing opening for guiding the second guidewire into the lumen of the catheter;

wherein the means for guiding comprises a proximally-facing funnel, the smaller opening of the funnel being attached to the proximally-facing opening in the guidewire lumen, the larger opening being proximal of the smaller opening; and wherein the funnel further comprises at least one perforation.

24. An improved guidewire exchange apparatus for use in facilitating the substitution of a second guidewire for a first guidewire positioned within a monorail catheter, the monorial catheter having a guidewire lumen passage therethrough and a proximally-facing opening in the lumen passages adapted to receive a guidewire, the improvement comprising means associated with the proximally-facing opening for guiding the second guidewire into the lumen of the catheter;

wherein the means for guiding comprises a proximally-facing funnel, the smaller opening of the funnel being attached to the proximally-facing opening in the guidewire lumen, the larger opening being proximal of the smaller opening;

wherein the funnel further comprises at least one perforation; and further comprising at least one slit extending from the large opening of the funnel at least partially to the smaller opening of the funnel.

25. A catheter exchange sheath for use in facilitating the substitution of a second catheter for a first catheter positioned within a guide catheter comprising:

an elongate sheath being of a length shorter than the guide catheter and having distal and proximal ends unattached to the guide catheter;

means associated with the proximal end of the sheath for guiding the second catheter into the elongate sheath;

means for advancing the sheath through a guide catheter;

wherein the means for guiding comprises a proximally-facing funnel, the smaller opening of the funnel being attached to the proximal end of the sheath, the larger opening being proximal of the smaller opening; and further comprising at least one slit extending from the larger opening of the funnel at least partially to the small opening of the funnel.

26. A catheter exchange sheath comprising;

a sheath adapted to be inserted into a guide catheter and having distal and proximal ends unattached to the guide catheter, the proximal end having a guide means attached thereto, the sheath further having a control means for advancing the sheath through and positioning the sheath within the guide catheter, the distal end of the sheath when positioned extending out of the guide catheter with the proximal end of the sheath being in the vicinity of the distal end of the guide catheter;

where the guide means comprises a funnel whose larger opening faces proximally of the sheath and whose small opening is secured to the proximal end of the sheath; and further comprising at least one slit extending from the larger opening of the funnel at least partially to the small opening of the funnel.

27. A catheter exchange sheath comprising:

a sheath adapted to be inserted into a guide catheter and having distal and proximal ends unattached to the guide catheter, the proximal end having a guide means attached thereto, the sheath further having a control means for advancing the sheath through and positioning the sheath within the guide catheter, the distal end of the sheath when positioned extending out of the guide catheter with the proximal end of the sheath being in the vicinity of the distal end of the guide catheter;

where the guide means comprises a funnel whose larger opening faces proximally of the sheath and whose small opening is secured to the proximal end of the sheath; and wherein the funnel further comprises at least one perforation.

28. An improved guidewire exchange apparatus for use in a facilitating the substitution of a second guidewire for a first guidewire positioned within a monorail catheter, the monorail catheter having a guide wire lumen passage therethrough and a proximally-facing opening in the lumen passage adapted to receive a guidewire, the improvement comprising means associated with the proximally-facing opening for guiding the second guidewire into the lumen of the catheter;

wherein the means for guiding comprises a proximally-facing funnel, the smaller opening of the funnel being attached to the proximally-facing opening the guidewire lumen, the larger opening being proximal of the smaller opening;

wherein the funnel further comprises at least one perforation;

wherein the monorail catheter is positioned in a guide catheter and wherein the diameter of the larger opening of the funnel approximates the diameter of the guide catheter; and further comprising at least one slit extending from the larger opening of the funnel at least partially to the smaller opening of the funnel.

* * * * *